United States Patent [19]

Anzai et al.

[11] Patent Number: 4,594,601
[45] Date of Patent: Jun. 10, 1986

[54] FLUORAN COMPOUNDS

[75] Inventors: Mitsutoshi Anzai; Masahiko Yamaguchi; Michihiro Gonda; Mikiko Kanasugi; Toshio Obara, all of Tokyo, Japan

[73] Assignee: Hodogaya Chemical Co., Ltd., Tokyo, Japan

[21] Appl. No.: 535,333

[22] Filed: Sep. 23, 1983

[30] Foreign Application Priority Data

Oct. 1, 1982 [JP] Japan .................... 57-171039
Jan. 22, 1983 [JP] Japan .................... 58-8094

[51] Int. Cl.$^4$ .................................. B41M 5/18
[52] U.S. Cl. .................................. 346/221; 428/195; 428/199; 428/913
[58] Field of Search .................. 428/913, 195, 199; 346/221

[56] References Cited

U.S. PATENT DOCUMENTS 4,439,512  3/1984  Ceintrey ................ 428/913 X
4,482,905 11/1984  Kaneko et al. ........ 346/221 X

FOREIGN PATENT DOCUMENTS 0116685  7/1982  Japan ...................... 428/913
0144787  9/1982  Japan ...................... 428/913
0202348 12/1982  Japan ...................... 428/913

Primary Examiner—Thomas J. Herbert
Attorney, Agent, or Firm—Oblon, Fisher, Spivak, McClelland & Maier

[57] ABSTRACT

A fluoran compound represented by general formula:

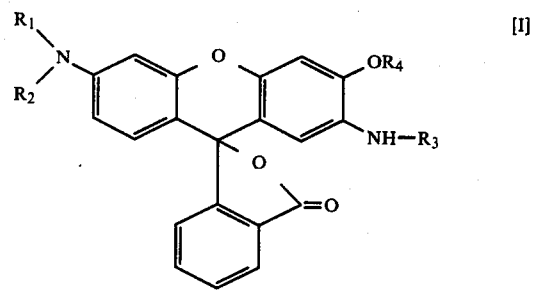

[I]

where each of $R_1$ and $R_2$ is a $C_1$–$C_4$ alkyl group, a cycloalkyl group or an aryl group, or $R_1$ and $R_2$ may form together with N a saturated ring, $R_3$ is a benzyl or phenyl group which may be substituted, and $R_4$ is a $C_1$–$C_4$ alkyl group.

8 Claims, No Drawings

FLUORAN COMPOUNDS

The present invention relates to novel fluoran compounds. More particularly, the invention relates to 2-substituted amino-3-alkoxy-6-di-substituted amino-fluoran compounds which are useful as color precursors for heat sensitive record sheets or electrical heat sensitive record sheets. Certain fluoran compounds have been disclosed in Japnanese Examined Patent Publications No. 2406/1973, No. 43296/1973, No. 32767/1974 and No.23204/1976, and Japanese Unexamined Patent Publication No. 34526/1974. These fluoran compounds are used as color precursors for heat sensitive record sheets or electrical heat sensitive record sheets. However, heat sensitive record sheets wherein these fluoran compounds are used as color precursors, have various drawbacks, for instance, in the developed color density, the initial color density, the color-development initiation temperature and the rising for color-development. Therefore, they cannot provide adequate properties required for heat sensitive record sheets. For instance, 2-anilino-3-methyl-6-diethylamino-fluoran disclosed in the above-mentioned Japanese Examined Patent Publications, tends to undergo partial color development during the preparation of heat sensitive record sheets, whereby the initial color density of the record sheets tends to be high. On the other hand, with a heat sensitive record sheet wherein 2-(2-chlorophenylamino)-6-diethylamino-fluoran is used, the initial color density is low, but the color-deveopment initiation temperature is too high and the rising for the color development is inadequate. Further, 2-anilino-3-methyl-6-N-methyl-N-cyclohexylamino-fluoran does not provide an adequate rising for color development.

The rising for color-development means a rising of a curve in a diagram of color density-color development temperature curve given by plotting color densities on the ordinate and color-development temperatures on the abscissas as a value given by multiplying 100 to $\tan\theta$ in the maximum slant of the curve.

The present inventors have conducted extensive researches for fluoran compounds to be used for heat sensitive record sheets which have no substantial slef-color development, a high developed color density, a low color-development initiation temperature and a high rising for color-development, and have finally found that 2-substituted amino-3-alkoxy-6-di-substituted amino-fluoran compounds have excellent properties to satisfy the above requirements.

Namely, the present invention provides fluoran compounds represented by general formula:

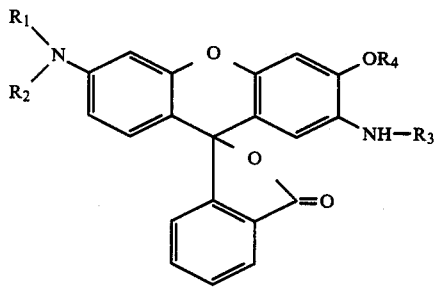

where each of $R_1$ and $R_2$ is a $C_1$–$C_4$ alkyl group, a cycloalkyl group or an aryl group, or $R_1$ and $R_2$ may form together with N a saturated ring, $R_3$ is a benzyl or phenyl group which may be substituted, and $R_4$ is a $C_1$–$C_4$ alkyl group.

The present invention also provides a heat sensitive record sheet which comprises a coated layer comprising a fluoran compound represented by the above general formula I.

Now, the present invention will be described in detail with reference to the preferred embodiments.

The fluoran compounds represented by the general formula I according to the present invention are colorless or slightly colored solids which are stable in air and which, when brought in contact with an acidic substance, immediately form coloring agents having a dark black color. The developed coloring agents have excellent storage stability and are therefore quite useful.

The fluoran compounds represented by the general formula I according to the present invention may be prepared by following method (1),(2) or (3).

(1) An aniline derivative represented by the general formula:

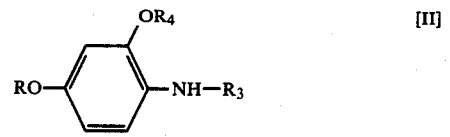

where R is a hydrogen atom or a $C_1$–$C_4$ alkyl group, and $R_3$ and $R_4$ are as defined above with respect to the general formula I, and a benzophenone compound represented by the general formula:

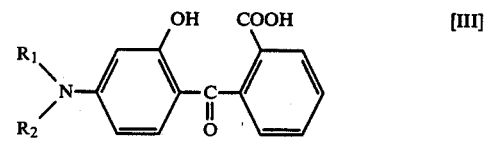

where $R_1$ and $R_2$ are as defined above with respect to the general formula I, are reacted in the presence of concentrated sulfuric acid at a temperature of from 0° to 80° C. for several hours. After the reaction, the reaction mixture is poured into water and then adjusted to a pH of from 8 to 10 with an addition of sodium hydroxide, whereupon the precipitates are collected by filtration. To the cake thus obtained, toluene and an aqueous solution containing from 5 to 10% of sodium hydroxide are added, and the mixture is stirred for from 1 to 3 hours under reflux, whereupon the toluene layer is separated by liquid separation, washed with water and then concentrated. The precipitated crystals are collected by filtration. The crystals are dried, whereby a slightly colored 2-substituted amino-3-alkoxy-6-di-substituted amino-fluoran represented by the general formula I is obtainable in high purity and high yield. If necessary, the product is recrystallized from a volatile organic solvent such as tolene, acetone, butylacetate or hexane.

(2) A 2-amino-3-alkoxy-6-di-substituted amino-fluoran represented by the general formula:

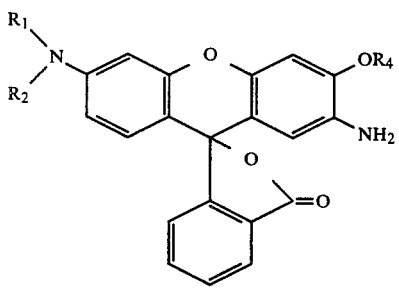

where $R_1$, $R_2$ and $R_4$ are defined above with respect to the general formula I, is reacted with a substituted benzyl chloride or a substituted benzyl bromide in a volatile organic inert solvent in the presence of an acid-binding agent such as sodium bicarbonate, or with a substituted bromobenzene or chlorobenzene in a volatile organic inert solvent in the presence of potassium carbonate by using copper powder and iodine as catalysts, whereby a 2-substituted amino-3-alkoxy-6-di-substituted amino-fluoran represented by the general formula I is obtainable.

(3) A 2-substituted amino-3-hydroxy-6-di-substituted amino-fluoran represented by the general formula:

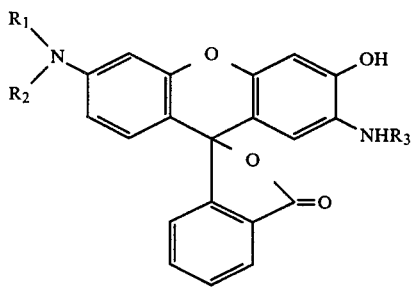

where $R_1$, $R_2$ and $R_3$ are as defined above with respect to the general formula I, is reacted with an alkylating agent such as dimethyl sulfate, methyl p-toluene sulfonate or methyl iodide in the presence of an alkali such as sodium hydroxide in water or in a volatile organic inert solvent, whereby a 2-substituted amino-3-alkoxy-6-di-substituted amino-fluoran represented by the general formula I is obtainable.

From the practical point of view, the method (1) is preferred.

As representative compounds of the above general formula I of the present invention, there may be mentioned 2-benzylamino-3-methoxy-6-diethylamino-fluoran, 2-benzylamino-3-methoxy-6-di-n-butylamino-fluoran, 2-benzylamino-3-methoxy-6-N-methyl-N-cyclohexylamino-fluoran, 2-anilino-3-methoxy-6-diethylamino-fluoran, 2-anilino-3-methoxy-6-N-methyl-N-cyclohexylamino-fluoran, 2-(2-methylphenylamino)-3-methoxy-6-diethylamino-fluoran, 2-(2-methylphenylamino)-3-methoxy-6-di-n-butylamino-fluoran, 2-(4-methylphenylamino)-3-methoxy-6-diethylamino-fluoran, 2-(4-methylphenylamino)-3-methoxy-6-di-n-butylaminofluoran, 2-(2-chlorophenylamino)-3-methoxy-6-diethylamino-fluoran, 2-(2-chlorophenylamino)-3-methoxy-6-di-n-buthylamino-fluoran, 2-(4-chlorophenylamino)-3-methoxy-6-diethylamino-fluoran, 2-(4-chlorophenylamino)-3-methoxy-6-di-n-butylamino-fluoran, 2-anilino-3-ethoxy-6-diethylamino-fluoran, 2-anilino-3-ethoxy-6-di-n-butylamino-fluoran, 2-anilino-3-ethoxy-6-N-methyl-N-cyclohexylamino-fluoran, 2-anilino-3-ethoxy-6-N-ethyl-N-p-tolylamino-fluoran, 2-(2-methylphenylamino)-3-ethoxy-6-diethylamino-fluoran, 2-(2-methylphenylamino)-3-ethoxy-6-di-n-butylamino-fluoran, 2-(4-methylphenylamino)-3-ethoxy-6-diethylamino-fluoran, 2-(4-methyphenylamino)-3-ethoxy-6-di-n-butylamino-fluoran, 2-(4-methylphenylamino)-3-ethoxy-6-N-ethyl-N-p-tolylamino-fluoran, 2-(4-chlorophenylamino)-3-ethoxy-6-diethylamino-fluoran, 2-(4-chlorophenylamino)-3-ethoxy-6-di-n-butylamino-fluoran, 2-(4-chlorophenylamino)-3-ethoxy-6-N-ethyl-N-p-tolylamino-fluoran, 2-anilino-3-methoxy-6-pyrrolidinyl-fluoran, 2-anilino-3-methoxy-6-N-ethyl-N-cyclohexylamino-fluoran, 2-anilino-3-propoxy-6-diethylamino-fluoran, 2-anilino-3-propoxy-6-di-n-butylamino-fluoran, 2-anilino-3-butoxy-6-diethylamino-fluoran, 2-anilino-3-butoxy-6-di-n-butylamino-fluoran.

As typical representatives of the aniline derivative represented by the general formula II to be used in the present invention, there may be mentioned N-benzyl-2,4-dimethoxyaniline, N-phenyl-2,4-dimethoxyaniline, N-(2-methylphenyl)-2,4-dimethoxyaniline, N-(4-methylphenyl)-2,4-dimethoxyaniline, N-(2-chlorophenyl)-2,4-dimethoxyaniline, N-(4-chlorophenyl)-2,4-dimethoxyaniline, N-benzyl-4-hydroxy-2-methoxyaniline, N-phenyl-4-hydroxy-2-methoxyaniline, N-phenyl-2,4-diethoxyaniline, N-(2-methylphenyl)-2,4-diethoxyaniline, N-(4-methylphenyl)-2,4-diethoxyaniline, N-(2-chlorophenyl)-2,4-diethoxyaniline, N-(4-chlorophenyl)-2,4-diethoxyaniline and N-phenyl-4-hydroxy-2-ethoxyaniline. Among the above aniline derivatives, those substituted by an alkoxy group at 4-position are preferred from the practical point of view.

As the benzophenone compound represented by the above general formula III to be used in the present invention, there may be mentioned 2-hydroxy-4-dimethylamino-2'-carboxy-benzophenone, 2-hydroxy-4-diethylamino-2'-carboxybenzophenone, 2-hydroxy-4-dipropylamino-2'-carboxybenzophenone, 2-hydroxy-4-dibutylamino-2'-carboxybenzophenone, 2-hydroxy-4-N-methyl-N-cyclohexylamino-2'carboxybenzophenone, 2-hydroxy-4-N-ethyl-N-p-tolylamino-2'-carboxybenzophenone, 2-hydroxy-4-pyrrolidinyl-2'-carboxybenzophenone and 2-hydroxy-4-piperidino-2'-carboxy-benzophenone.

As representatives of the 2-amino-3-alkoxy-6-di-substituted amino-fluoran represented by the above general formula IV to be used in the present invention, there may be mentioned 2-amino-3-methoxy-6-dimethylamino-fluoran, 2-amino-3-methoxy-6-diethylamino-fluoran, 2-amino-3-methoxy-6-dipropylamino-fluoran, 2-amino-3-methoxy-6-dibutylamimo-fluoran, 2-amino-3-methoxy-6-N-methyl-N-cyclohexylamino-fluoran, 2-amino-3-methoxy-6-N-ethyl-N-p-tolylamino-fluoran, 2-amino-3-methoxy-6-pyrrolidinyl-fluoran, 2-amino-3-methoxy-6-piperidino-fluoran, 2-amino-3-ethoxy-6-dimethylamino-fluoran, 2-amino-3-ethoxy-6-diethylamino-fluoran, 2-amino-3-propoxy-6-dipropylamino-fluoran, 2-amino-3-propoxy-6-dibutylamino-fluoran, 2-amino-3-butoxy-6-N-methyl-N-cyclohexylamino-fluoran and 2-amino-3-butoxy-6-N-ethyl-N-p-tolylamino-fluoran.

As representatives of the 2-substituted amino-3-hydroxy-6-di-substituted amino-fluoran represented by the above general formula V to be used in the present invention, there may be mentioned 2-benzylamino-3- hydroxy-6-diethylamino-fluoran, 2-anilino-3-hydroxy-6-dimethylamino-fluoran, 2-anilino-3-hydroxy-6-diethylamino-fluoran, 2-anilino-3-hydroxy-6-dipropylamino-fluoran, 2-anilino-3-hydroxy-6-dibutylamino-fluoran, 2-anilino-3-hydroxy-6-N-methyl-N-cyclohexylamino-fluoran, 2-anilino-3-hydroxy-6-N-ethyl-N-p-tolylamino-fluoran, 2-(4-methylphenylamino)-3-hydroxy-6-diethylamino-fluoran, 2-(2-methylphenylamino)-3-hydroxy-6-diethylamino-fluoran, 2-(4-chlorophenylamino)-3-hydroxy-6-diethylamino-fluoran and 2-(2-chlorophenylamino)-3-hydroxy-6-diethylamino-fluoran.

As the substituted benzylchloride or the substituted benzylbromide to be used in the present invention, there may be mentioned benzylchloride, benzylbromide, 2-chlorobenzylchloride, 2-chlorobenzylbromide, 3-chlorobenzylchloride, 4-chlorobenzylchloride, 2-methylbenzylchloride, 4-methylbenzylchloride, 3-methylbenzylchloride and 2-methylbenzylbromide.

As the substituted bromobenzene or substituted chlorobenzene to be used in the present invention, there may be mentioned 2-bromochlorobenzene, o-dichlorobenzene, 3-bromochlorobenzene, 4-bromochlorobenzene, bromobenzene, 2-bromotoluene, 4-bromotoluene or 3-bromotoluene.

As the condensing agent to be used in the present invention, there may be mentioned concentrated sulfuric acid, acetic acid anhydride, phosphoric acid, polyphosphoric acid, phosphorus oxychloride and zinc chloride. From the practical point of view, it is preferred to use concentrated sulfuric acid which serves as a solvent for a benzophenone compound represented by the above general formula III and at the same time serves as a condensing agent.

Now, the present invention will be described in further detail with reference to Examples for the preparation of typical 2-substituted amino-3-alkoxy-6-di-substituted amino-fluoran compounds of the present invention and Application Examples

EXAMPLE 1

2-Benzylamino-3-methoxy-6-diethylamino-fluoran (Compound No. A)

To 150 g of 95% sulfuric acid, 12.5 g of 2-hydroxy-4-diethylamino-2'-carboxy-benzophenone was added and completely dissolved at a temperature of about 20° C., and then 9.7 g of N-benzyl-2,4-dimethoxyaniline was added and reacted therewith at a temperature of from 10° to 20° C. for 24 hours. After the reaction, the reaction mixture was poured into 1 liter of ice water and then adjusted to a pH of from 7 to 8 by an addition of 10% sodium hydroxide aqueous solution, whereupon the precipitates were collected by filtration. To the cake thus obtained, 300 ml of toluene and 150 ml of a 10% sodium hydroxide aqueous solution were added, and the mixture was stirred for 2 hours under reflux. Then, the toluene layer was separated by liquid separation, then washed with water, concentrated to dryness and solidified by an addition of hexane. The solid thereby obtained was dried to obtain 20.5 g of slightly pink 2-benzylamino-3-methoxy-6-diethylamino-fluoran. The melting point of this product was from 72° to 76° C. Further, this product had $\lambda_{max}$ at 439 nm (a molecular extinction coefficient (hereinafter referred to simply as "MEC"): $1.42 \times 10^4$) and at 583 nm (MEC: $3.91 \times 10^4$) as measured in 95% acetic acid. A solution of this product in toluene was colorless. When brought in contact with silica gel, the product readily underwent color-development and turned purplish black.

The N-benzyl-2,4-dimethoxyaniline used as a starting material was prepared in the following manner.

Into 150 ml of ethanol, 30.6 g of 2,4-dimethoxyaniline and 21.2 g of benzaldehyde were dissolved, and 2 g of acetic acid was added. The mixture was reacted at a temperature of from 50° to 60° C. for 4 hours. The reaction solution was poured into 500 ml of water and extracted with 300 ml of toluene. The toluene solution was separated by liquid separation, then washed with water and concentrated to dryness. The oily product thereby obtained was dissolved into 150 ml of ethanol, and 11.3 g of sodium boro-hydride was added in 2 hours at a temperature of from 30° to 40° C. and reacted therewith. Further, the mixture was stirred for one hour at a temperature of 40° C. The reaction mixture was poured into 1 liter of water and extracted with 500 ml of toluene. The toluene layer was washed with water, concentrated and purified by distillation under reduced pressure, whereby 40.9 g of N-benzyl-2,4-dimethoxyaniline was obtained. The product was a liquid having a boiling point of from 166° to 168° C./2 mmHg.

EXAMPLE 2

2-Benzylamino-3-methoxy-6-di-n-butylamino-fluoran (Compound No. B)

To 70 g of 95% sulfuric acid, 7.4 g of 2-hydroxy-4-di-n-butylamino-2'-carboxy-benzophenone and 4.9 g of N-benzyl-2,4-dimethoxyaniline were added and reacted in the same manner as in Example 1, whereby 9.8 g of slightly purple 2-benzylamino-3-methoxy-6-di-n-butylamino-fluoran was obtained. The melting point of this product was from 134° to 136° C. The product had $\lambda_{max}$ at 443 nm (MEC: $1.59 \times 10^4$) and at 587 nm (MEC: $3.95 \times 10^4$) as measured in 95% acetic acid. A solution of this product in toluene was colorless. When brought in contact with silica gel, the product readily underwent color-development and turned blackish purple.

EXAMPLE 3

2-Benzylamino-3-methoxy-6-N-methyl-N-cyclohexylamino-fluoran (Compound No. C)

To 70 g of 95% sulfuric acid, 7.1 g of 2-hydroxy-4-N-methyl-N-cycolhexylamino-2'-carboxy-benzophenone and 4.9 g of N-benzyl-2,4-dimethoxyaniline were added and reacted in the same manner as in Example 1. The product was recrystallized from toluene, whereby 8.3 g of slightly purple 2-benzyl-3-methoxy-6-N-methyl-N-cyclohexylamino-fluoran was obtained. The melting point of this product was from 210° to 211.5° C. The product had $\lambda_{max}$ at 443 nm (MEC: $1.55 \times 10^4$) and at 587 nm (MEC: $3.94 \times 10^4$) as measured in 95% acetic acid. A solution of this product in toluene was colorless. When brought in contact with silica gel, the product readily underwent color-development and turned blackish purple.

EXAMPLE 4

2-Anilino-3-methoxy-6-diethylamino-fluoran (Compound No. D)

To 150 g of 95% sulfuric acid, 15.7 g of 2-hydroxy-4-diethylamino-2'-carboxy-benzophenone and 11.5 g of N-phenyl-2,4-dimethoxy aniline were added and reacted in the same manner as in Example 1. The product was recrystallized from toluene, whereby 13.0 g of white 2-anilino-3-methoxy-6-diethylamino-fluoran was obtained. The melting point of this product was from 104° to 104.5°C. The product had $\lambda_{max}$ at 449 nm (MEC: $1.46 \times 10^4$) and at 591 nm (MEC: $3.11 \times 10^4$) as measured in 95% acetic acid. A solution of this product in toluene was colorless. When brought in contact with silica gel, the product readily underwent color-development and turned bluish black.

The N-phenyl-2,4-dimethoxyaniline used as starting material was prepared in the following manner.

To a mixture of 58.5 g of N-acetyl-2,4-dimethoxyaniline and 70.7 g of bromobenzene, 29 g of anhydrous potassium carbonate, 2.1 g of copper powder and 0.8 g of iodine were added and reacted at a temperature of from 170° to 180° C. for 20 hours. Then, to this reaction mixture, 30 g of potassium hydroxide and 100 ml of isoamyl alcohol were added and reacted at a temperature of from 120° to 130° C. for 3 hours. To this reaction mixture, 300 ml of toluene was added, and the toluene layer was separated by liquid separation, washed with water, concentrated and then purified by distillation under reduced pressure, whereby 40 g of oily N-phenyl-2,4-dimethoxyaniline was obtained. The boiling point of this product was from 161° to 164° C./2 mmHg.

EXAMPLE 5

2-Anilino-3-methoxy-6-di-n-butylamino-fluoran (Compound No. E)

To 150 g of 95% sulfuric acid, 18.5 g of 2-hydroxy-4-di-n-butylamino-2'-carboxy-benzophenone and 11.5 g of N-phenyl-2,4-dimethoxyaniline were added and reacted in the same manner as in Example 1. The product was recrystallized from toluene, whereby 20.9 g of white 2-anilino-3-methoxy-6-di-n-butylamino-fluoran was obtained. The melting point of this product was from 169° to 172° C. The product had $\lambda_{max}$ at 451 nm (MEC: $1.52 \times 10^4$) and at 593 nm (MEC: $3.29 \times 10^4$) as measured in 95% acetic acid. A solution of this product in toluene was colorless. When brought in contact with silica gel, the product readily underwent color-development and turned bluish black.

EXAMPLE 6

2-Anilino-3-methoxy-6-N-methyl-N-cyclohexylamino-fluoran (Compound No. F)

To 60 g of 95% sulfuric acid, 7.1 g of 2-hydroxy-4-N-methyl-N-cyclohexylamino-2'-carboxybenzophenone and 4.6 g of N-phenyl-2,4-dimethoxyaniline were added and reacted in the same manner as in Example 1. The product was recrystallized from acetone, whereby 4.4 g of white 2-anilino-3-methoxy-6-N-methyl-N-cyclohexylamino-fluoran was obtained. The melting point of this product was from 201° to 203.5° C. The product had $\lambda_{max}$ at 450 nm (MEC: $1.63 \times 10^4$) and at 593 nm (MEC: $3.45 \times 10^4$) as measured in 95% acetic acid. A solution of this product in toluene was colorless. When brought in contact with silica gel, the product readily underwent color-development and turned bluish black.

EXAMPLE 7

2-Anilino-3-methoxy-6-N-ethyl-N-p-tolylamino-fluoran (Compound No. G)

To 60 g of 95% sulfuric acid, 7.5 g of 2-hydroxy-4-N-ethyl-N-p-tolylamino-2'-carboxy-benzophenone and 4.6 g of N-phenyl-2,4-dimethoxyaniline were added and reacted in the same manner as in Example 1. The product was recrystallized from toluene, whereby 6.8 g of white 2-anilino-3-methoxy-6-N-ethyl-N-p-tolylamino-fluoran was obtained. The melting point of this product was from 196° to 199° C. The product had $\lambda_{max}$ at 453 nm (MEC: $1.82 \times 10^4$) and at 595 nm (MEC: $3.19 \times 10^4$) as measured in 95% acetic acid. A solution of this product in toluene was colorless. When brought in contact with silica gel, the product readily underwent color-development and turned bluish black.

EXAMPLE 8

2-(2-Methylphenylamino)-3-methoxy-6-diethylamino-fluoran (Compound No. H)

To 150 g of 95% sulfuric acid, 15.7 g of 2-hydroxy-4-diethylamino-2'-carboxy-benzophenone and 12.2 g of N-(2-methylphenyl)-2,4-dimethoxyaniline were added and reacted in the same manner as in Example 1. The product was recrystallized from toluene, whereby 18.7 g of white 2-(2-methylanilino)-3-methoxy-6-diethylamino-fluoran was obtained. The melting point of this product was from 124° to 127° C. The product had $\lambda_{max}$ at 441 nm (MEC: $1.40 \times 10^4$) and at 586 nm (MEC: $3.18 \times 10^4$) as measured in 95% acetic acid. A solution of this product in toluene was colorless. When brought in contact with silica gel, the product readily underwent color-development and turned purplish black.

The N-(2-methylphenyl)-2,4-dimethoxyaniline used as a starting material was prepared in the same manner as in Example 4 by using N-acetyl-2,4-dimethoxyaniline and 2-bromotoluene as the starting materials. The boiling point of the N-(2-methylphenyl)-2,4-dimethoxyanililne was from 172° to 175° C./2 mmHg.

EXAMPLE 9

2-(2-Methylphenylamino)-3-methoxy-6-di-n-butylamino-fluoran (Compound No. I)

To 150 g of 95% sulfuric acid, 18.5 g of 2-hydroxy-4-di-n-butylamino-2'-carboxy-benzophenone and 12.2 g of N-(2-methylphenyl)-2,4-dimethoxyaniline were added and reacted in the same manner as in Example 1. The product was recrystallized from toluene, whereby 18.3 g of white 2-(2-methylphenylamino)-3-methoxy-6-di-n-butylamino-fluoran was obtained. The melting point of this product was from 139° to 142° C. The product had $\lambda_{max}$ at 444 nm (MEC: $1.57 \times 10^4$) and at 588 nm (MEC: $3.64 \times 10^4$) as measured in 95% acetic acid. A solution of this product in toluene was colorless. When brought in contact with silica gel, the product readily underwent color-development and turned purplish black.

EXAMPLE 10

2-(4-Methylphenylamino)-3-methoxy-6-diethylamino-fluoran (Compound No. J)

To 150 g of 95% sulfuric acid, 15.7 g of 2-hydroxy-4-diethylamino-2'-carboxy-benzophenone and 12.2 g of N-(4-methylphenyl)-2,4-dimethoxyaniline were added and reacted in the same manner as in Example 1. The product was recrystallized from acetone, whereby 22.3 g of white 2-(4-methylphenylamino)-3-methoxy-6-diethylamino-fluoran was obtained. The melting point of this product was from 141° to 145° C. The product had $\lambda_{max}$ at 453 nm (MEC: $1.40 \times 10^4$) and at 595 nm (MEC: $2.58 \times 10^4$) as measured in 95% acetic acid. A solution of this product in toluene was colorless. When brought in contact with silica gel, the product readily underwent color-development and turned black.

The N-(4-methylphenyl)-2,4-dimethoxyaniline used as a starting material was prepared in the same manner as in Example 4 by using N-acetyl-2,4-dimethoxyaniline and 4-bromotoluene as the starting materials. The boiling point of the N-(4-methylphenyl)-2,4-dimethoxyanililne was from 173° to 175° C./2 mmHg.

EXAMPLE 11

2-(4-Methylphenylamino)-3-methoxy-6-di-n-butylamino-fluoran (Compound No. K)

To 150 g of 95% sulfuric acid, 18.5 g of 2-hydroxy-4-di-n-butylamino-2'-carboxy-benzophenone and 12.2 g of N-(4-methylphenyl)-2,4-dimethoxyaniline were added and reacted in the same manner as in Example 1. The product was recrystallized from toluene, whereby 15.6 g of white 2-(4-methylphenylamino)-3-methoxy-6-di-n-butylamino-fluoran was obtained. The melting point of this product was from 106° to 109° C. The product had $\lambda_{max}$ at 455 nm (MEC: $1.65 \times 10^4$) and at 600 nm (MEC: $3.14 \times 10^4$) as measured in 95% acetic acid. A solution of this product in toluene was colorless. When brought in contact with silica gel, the product readily underwent color-development and turned bluish black.

EXAMPLE 12

2-(2-Chlorophenylamino)-3-methoxy-6-diethylamino-fluoran (Compound No. L)

To 150 g of 95% sulfuric acid, 15.7 g of 2-hydroxy-4-diethylamino-2'-carboxy-benzophenone and 13.2 g of N-(2-chlorophenyl)-2,4-dimethoxyaniline were added and reacted in the same manner as in Example 1. The product was recrystallized from toluene, whereby 13.4 g of white 2-(4-chlorophenylamino)-3-methoxy-6-diethylamino-fluoran was obtained. The melting point of this product was from 121° to 125° C. The product had $\lambda_{max}$ at 437 nm (MEC: $1.29 \times 10^4$) and at 577 nm (MEC: $3.63 \times 10^4$) as measured in 95% acetic acid. A solution of this product in toluene was colorless. When brought in contact with silica gel, the product readily underwent color-development and turned dark red.

The N-(2-chlorophenyl)-2,4-dimethoxyaniline used as a starting material was prepared in the same manner as in Example 4 by using N-acetyl-2,4-dimethoxyaniline and 2-bromochlorobenzene as the starting materials. The N-(2-chlorophenyl)-2,4-dimethoxyaniline was an oil having a boiling point of from 170° to 177° C./2 mmHg.

EXAMPLE 13

2-(2-Chlorophenylamino)-3-methoxy-6-di-n-butylamino-fluoran (Compound No. M)

To 125 g of 95% sulfuric acid, 14.8 g of 2-hydroxy-4-di-n-butylamino-2'-carboxy-benzophenone and 10.6 g of N-(2-chlorophenyl)-2,4-dimethoxyaniline were added and reacted in the same manner as in Example 1. The product was recrystallized from toluene, whereby 12.2 g of white 2-(2-chlorophenylamino)-3-methoxy-6-di-n-butylamino-fluoran was obtained. The melting point of this product was from 105° to 107° C. The product had $\lambda_{max}$ at 440 nm (MEC: $1.30 \times 10^4$) and at 580 nm (MEC: $3.78 \times 10^4$) as measured in 95% acetic acid. A solution of this product in toluene was colorless. When brought in contact with silica gel, the product readily underwent color-development and turned dark red.

EXAMPLE 14

2-(4-Chlorophenylamino)-3-methoxy-6-diethylamino-fluoran (Compound No. N)

To 150 g of 95% sulfuric acid, 15.7 g of 2-hydroxy-4-diethylamino-2'-carboxy-benzophenone and 13.2 g of N-(4-chlorophenyl)-2,4-dimethoxyaniline were added and reacted in the same manner as in Example 1. The product was recrystallized from toluene, whereby 20.7 g of white 2-(4-chlorophenylamino)-3-methoxy-6-diethylamino-fluoran was obtained. The melting point of this product was from 123° to 127° C. The product had $\lambda_{max}$ at 449 nm (MEC: $1.34 \times 10^4$) and at 587 nm (MEC: $2.95 \times 10^4$) as measured in 95% acetic acid. A solution of this product in toluene was colorless. When brought in contact with silica gel, the product readily underwent color-development and turned purplish black.

The N-(4-chlorophenyl)-2,4-dimethoxyaniline used as a starting material was prepared in the same manner as in Example 4 by using N-acetyl-2,4-dimethoxyaniline and 4-bromochlorobenzene as the starting materials. The N-(4-chlorophenyl)-2,4-dimethoxyaniline was an oil having a boiling point of from 178° to 180° C./2 mmHg.

EXAMPLE 15

2-(4-Chlorophenylamino)-3-methoxy-6-di-n-butylamino-fluoran (Compound No. 0)

To 150 g of 95% sulfuric acid, 18.5 g of 2-hydroxy-4-di-n-butylamino-2'-carboxy-benzophenone and 13.2 g of N-(4-chlorophenyl)-2,4-dimethoxyaniline were added and reacted in the same manner as in Example 1. The product was recrystallized from toluene, whereby 18.0 g of white 2-(4-chlorophenylamino)-3-methoxy-6-di-n-butylamino-fluoran 91° to 95° C. The product had $\lambda_{max}$ at 449 nm (MEC: $1.46 \times 10^4$) and at 590 nm (MEC: $3.36 \times 10^4$) as measured in 95% acetic acid. A solution of this product in toluene was colorless. When brought in contact with silica gel, the product readily underwent color-development and turned bluish black.

EXAMPLE 16

2-Anilino-3-ethoxy-6-diethylamino-fluoran (Compound No. P)

To 100 g of 95% sulfuric acid, 9.4 g of 2-hydroxy-4-diethylamino-2'-carboxy-benzophenone was added and completely dissolved at a temperature of about 20° C., and then 7.7 g of N-phenyl-2,4-diethoxyaniline was added and reacted therewith at a temperature from 10° to 20° C. for 24 hours. After the reaction, the reaction mixture was poured into 700 ml of ice water and adjusted to pH of from 7 to 8 by an addition of a 10% sodium hydroxide aqueous solution, whereupon the precipitates were collected by filtration. To the cake thereby obtained, 300 ml of toluene and 150 ml of a 10% sodium hydroxide aqueous solution were added, and the mixture was stirred for 2 hours under reflux. Then, the toluene layer was separated by liquid separation, washed with water, concentrated to dryness and solidified by an addition of hexane. The solidified product was dried to obtain 12.1 g of slightly pink 2-anilino-3-ethoxy-6-diethylamino-fluoran. The melting point of this product was from 84° to 88° C. The product had $\lambda_{max}$ at 452 nm (MEC: $1.44 \times 10^4$) and at 593 nm (MEC: $2.93 \times 10^4$) as measured in 95% acetic acid. A solution of this product in toluene was colorless. When brought in contact in with silica gel, the product readily underwent color-development and turned bluish black.

The N-phenyl-2,4-diethoxyaniline used as starting material was prepared in the following manner.

To a mixture of 66.9 g of N-acetyl-2,4-diethoxyaniline and 70.7 g of bromobenzene, 29 g of anhydrous potassium carbonate, 2.1 g of copper powder and 0.8 g of iodine were added, and the mixture was reacted at a temperature of from 170° to 180° C. for 20 hours. Then, to this reaction mixture, 30 g of potassium hydroxide and 100 ml of isoamylalcohol were added, and the mixture was reacted at a temperature from 120° to 130° C. for 3 hours. Then, 300 ml of toluene was added thereto. The toluene layer was washed with water, separated by liquid separation, concentrated and then purified by distillation under reduced pressure, whereby 54 g of oily N-phenyl-2,4-di-ethoxyaniline was obtained. The boiling point of this product was from 180° to 185° C./3 mmHg.

EXAMPLE 17

2-Anilino-3-ethoxy-6-di-n-butylamino-fluoran (Compound No. Q)

To 100 g of 95% sulfuric acid, 11.1 g of 2-hydroxy-4-di-n-butylamino-2'-carboxy-benzophenone and 7.7 g of N-phenyl-2,4-diethoxyaniline were added and reacted in the same manner as in Example 16. The product was recrystallized from cyclohexene, whereby 11.8 g of white 2-anilino-3-ethoxy-6-di-n-butylamino-fluoran was obtained. The melting point of this product was from 125° to 128° C. The product had $\lambda_{max}$ at 453 nm (MEC: $1.48 \times 10^4$) and at 597 nm (MEC: $3.17 \times 10^4$) as measured in 95% acetic acid. A solution of this product in toluene was colorless. When brought in contact with silica gel the product readily underwent color-development and turned bluish black.

EXAMPLE 18

2-Anilino-3-ethoxy-6-N-methyl-N-cyclohexylamino-fluoran (Compound No. R)

To 100 g of 95% sulfuric acid, 10.6 g of 2-hydroxy-4-N-methyl-N-cyclohexylamino-2'-carboxybenzophenone and 7.7 g of N-phenyl-2,4-diethoxyaniline were added and reacted in the same manner as in Example 16. The product was recrystallized from n-octylchloride, whereby 9.0 g of white 2-anilino-3-ethoxy-6-N-methyl-N-cyclohexylamino-fluoran was obtained. The melting point of this product was from 169° to 173° C.. The product had $\lambda_{max}$ at 452 nm (MEC: $1.47 \times 10^4$) and at 597 nm (MEC: $3.16 \times 10^4$) as measured in 95% acetic acid. A solution of this product in toluene was colorless. When brought in contact with silica gel, the product readily underwent color-development and turned bluish black.

EXAMPLE 19

2-Anilino-3-ethoxy-6-N-ethyl-N-p-tolylamino-fluoran (Compound No. S)

To 100 g of 95% sulfuric acid, 11.3 g of 2-hydroxy-4-N-ethyl-N-p-tolylamino-2'-carboxy-benzophenone and 7.7 g of N-phenyl-2,4-diethoxyaniline were added and reacted in the same manner as in Example 16. The product was recrystallized from n-butylchloride, whereby 12.7 g of white 2-anilino-3-ethoxy-6-N-ethyl-N-p-tolylamino-fluoran was obtained. The melting point of this product was from 148° to 152° C. The product had $\lambda_{max}$ at 453 nm (MEC: $1.92 \times 10^4$) and at 595 nm (MEC: $3.42 \times 10^4$) as measured in 95% acetic acid. A solution of this product in toluene was colorless. When brought in contact with silica gel, the product readily underwent color-development and turned bluish black.

EXAMPLE 20

2-(2-Methylphenylamino)-3-ethoxy-6-diethylamino-fluoran (Compound No. T)

To 75 g of 95% sulfuric acid, 6.9 g of 2-hydroxy-4-diethylamino-2'-carboxy-benzophenone and 5.4 g of N-(2-methylphenyl)-2,4-diethoxyaniline were added and reacted in the same manner as in Example 16. The product was recrystallized, whereby 7.8 g of white 2-(2-methylphenylamino)-3-ethoxy-6-diethylamino-fluoran was obtained. The melting point of this product was from 197.5° to 200° C. The product had $\lambda_{max}$ at 443 nm (MEC: $1.46 \times 10^4$) and at 586 nm (MEC: $3.46 \times 10^4$) as measured in 95% acetic acid. A solution of this product in toluene was colorless. When brought in contact with silica gel, the product readily underwent color-development and turned purplish black.

The N-(2-methylphenyl)-2,4-diethoxyaniline used as a starting material was prepared in the same manner as in Example 16 by using N-acetyl-2,4-diethoxyaniline and 2-bromotoluene as the starting materials. The boiling point of the N-(2-methylphenyl)-2,4-diethoxyaniline was from 170° to 172° C./0.5 mmHg.

EXAMPLE 21

2-(2-Methyphenylamino)-3-ethoxy-6-di-n-butylamino-fluoran (Compound No. U)

To 75 g of 95% sulfuric acid, 8.1 g of 2-hydroxy-4-di-n-butylamino-2'-carboxy-benzophenone and 5.4 g of N-(2-methylphenyl)-2,4-diethoxyaniline were added and reacted in the same manner as in Example 16. The product was recrystallized, whereby 8.1 g of white 2-(2-methylphenylamino)-3-ethoxy-6-di-n-butylamino-fluoran was obtained. The melting point of this product was from 125 to 130° C. The product had $\lambda_{max}$ at 444 nm (MEC: $1.49 \times 10^4$) and at 589 nm (MEC: $3.63 \times 10^4$) as measured in 95% acetic acid. A solution of this product in toluene was colorless. When brought in contact with silica gel, the product readily underwent color-development and turned purplish black.

EXAMPLE 22

2-(4-Methylphenylamino)-3-ethoxy-6-diethylamino-fluoran (Compound No. V)

To 100 g of 95% sulfuric acid, 10.3 g of 2-hydroxy-4-diethylamino-2'-carboxy-benzophenone and 8.1 g of N-(4-methtylphenyl)-2,4-diethoxyaniline were added and reacted in the same manner as in Example 16. The product was recrystallized, whereby 11.7 g of white 2-(4-methylphenylamino)-3-ethoxy-6-diethylamino-fluoran was obtained. The melting point of this product was from 110° to 113° C. The product had $\lambda_{max}$ at 454 nm (MEC: $1.47 \times 10^4$) and at 597 nm (MEC: $2.85 \times 10^4$) as measured in 95% acetic acid. A solution of this product in toluene was colorless. When brought in contact with silica gel, the product readily underwent color-development and turned purplish black.

The N-(4-methylphenyl)-2,4-diethoxyaniline used as a starting material was prepared in the same manner as in Example 16 by using N-acetyl-2,4-diethoxyaniline and 4-bromotoluene as the starting materials. The boiling point of the N-(4-methylphenyl)-2,4-diethoxyaniline was from 195° to 197° C./3 mmHg.

EXAMPLE 23

2-(4-Methylphenylamino)-3-ethoxy-6-di-n-butylamino-fluoran (Compound No. W)

To 100 g of 95% sulfuric acid, 12.2 g of 2-hydroxy-4-di-n-butylamino-2'-carboxy-benzophenone and 8.1 g of N-(4-methylphenyl)-2,4-diethoxyaniline were added and reacted in the same manner as in Example 16. The product was recrystallized, whereby 11.4 g of slightly pink 2-(4-methylphenylamino)-3-ethoxy-6-di-n-butylamino-fluoran was obtained. The melting point of this product was from 137° to 141° C. The product had $\lambda_{max}$ at 454 nm (MEC: $1.57 \times 10^4$) and at 597 nm (MEC: $3.14 \times 10^4$) as measured in 95% acetic acid. A solution of this product in toluene was colorless. When brought in contact with silica gel, the product readily underwent color-development and turned purplish black.

EXAMPLE 24

2-(4-Methylphenylamino)-3-ethoxy-6-N-ethyl-N-p-tolylamino-fluoran (Compound No. X)

To 100 g of 95% sulfuric acid, 12.3 g of 2-hydroxy-4-N-ethyl-N-p-tolylamino-2'-carboxy-benzophenone and 8.1 g of N-(4-methylphenyl)-2,4-diethoxyaniline were added and reacted in the same manner as in Example 16. The product was recrystallized from toluene, whereby 13.3 g of white 2-(4-methylphenylamino)-3-ethoxy-6-N-ethyl-N-p-tolylamino-fluoran was obtained. The melting point of this product was from 155° to 158° C. The product had $\lambda_{max}$ at 459 nm (MEC: $1.84 \times 10^4$) and at 601 nm (MEC: $2.92 \times 10^4$) as measured in 95% acetic acid. A solution of this product in toluene was colorless. When brought in contact with silica gel, the product readily underwent color-development and turned greenish black.

EXAMPLE 25

2-(4-Chlorophenylamino)-3-ethoxy-6-diethylamino-fluoran (Compound No. Y)

To 100 g of 95% sulfuric acid, 9.4 g of 2-hydroxy-4-diethylamino-2'-carboxy-benzophenone and 8.8 g of N-(4-chlorophenyl)-2,4-diethoxyaniline were added and reacted in the same manner as in Example 16. The product was recrystallized, whereby 13.5 g of white 2-(4-chlorophenylamino)-3-ethoxy-6-diethylamino-fluoran was obtained. The melting point of this product was from 136° to 140° C. The product had $\lambda_{max}$ at 448 nm (MEC: $1.55 \times 10^4$) and at 589 nm (MEC: $3.50 \times 10^4$) as measured in 95% acetic acid. A solution of this product in toluene was colorless. When brought in contact with silica gel, the product readily underwent color-development and turned bluish black.

The N-(4-chlorophenyl)-2,4-diethoxyaniline used as a starting material was prepared in the same manner as in Example 16 by using N-acetyl-2,4-diethoxyaniline and 4-bromochlorobenzene as the starting materials. The N-(4-chlorophenyl)-2,4-diethoxyaniline had a boiling point of from 188° to 190° C./0.5 mmHg.

EXAMPLE 26

2-(4-Chlorophenylamino)-3-ethoxy-6-di-n-butylamino-fluoran (Compound No. Z)

To 100 g of 95% sulfuric acid, 11.1 g of 2-hydroxy-4-di-n-butylamino-2'-carboxy-benzophenone and 8.8 g of N-(4-chlorophenyl)-2,4-diethoxyaniline were added and reacted in the same manner as in Example 16. The product was recrystallized, whereby 15.4 g of slightly pink 2-(4-chlorophenylamino)-3-ethoxy-6-di-n-butylamino-fluoran was obtained. The melting point of this product was from 116° to 120° C. The product had $\lambda_{max}$ at 449 nm (MEC: $1.39 \times 10^4$) and at 590 nm (MEC: $3.48 \times 10^4$) as measured in 95% acetic acid. A solution of this product in toluene was colorless. When brought in contact with silica gel, the product readily underwent color development and turned bluish black.

EXAMPLE 27

2-(4-Chlorophenylamino)-3-ethoxy-6-N-ethyl-N-p-tolylamino-fluoran (Compound No. AA)

To 100 g of 95% sulfuric acid, 12.3 g of 2-hydroxy-4-N-ethyl-N-p-tolylamino-2'-carboxy-benzophenone and 8.8 g of N-(4-chlorophenyl)-2,4-diethoxyaniline were added and reacted in the same manner as in Example 16. The product was recrystallized from toluene, whereby 13.5 g of white 2-(4-chlorophenylamino)-3-ethoxy-6-N-ethyl-N-p-tolylamino-fluoran was obtained. The melting point of this product was from 144° to 147.5° C. The product had $\lambda_{max}$ at 453 nm (MEC: $1.68 \times 10^4$) and at 593 nm (MEC: $3.33 \times 10^4$) as measured in 95% acetic acid. A solution of this product in toluene was colorless. When brought in contact with silica gel, the product readily underwent color-development and turned bluish black.

EXAMPLE 28

2-(4-Chlorophenylamino)-3-methoxy-6-N-ethyl-N-p-tolylamino-fluoran (Compound No. AB)

To 100 g of 95% sulfuric acid, 12.4 g of 2-hydroxy-4-N-ethyl-N-p-tolylamino-2'-carboxy-benzophenone and 8.0 g of N-(4-chlorophenyl)-2,4-dimethoxyaniline were added and reacted in the same manner as in Example 1. The product was recrystallized from toluene, whereby 12.9 g of white 2-(4-chlorophenylamino)-3-methoxy-6-N-ethyl-N-p-tolylamino-fluoran was obtained. The melting point of this product was from 209° to 213° C. The product had $\lambda_{max}$ at 454 nm (MEC: $1.66 \times 10^4$) and at 591 nm (MEC: $3.13 \times 10^4$) as measured in 95% acetic acid. A solution of this product in toluene was colorless. When brought in contact with silica gel, the product readily underwent color-development and turned bluish black.

APPLICATION EXAMPLE 1

To 2.0 g of Compound A prepared in Example 1, 20 g of water and 20 g of an aqueous solution containing 10% by weight of polyvinyl alcohol were added. The mixture was slowly dispersed and mixed in a ball mill at room temperature for 24 hours, whereby a colorless slurry was obtained wherein the particle size of the compound was about 3 μm. On the other hand, 7 g of bisphenol A was added to 10 g of water and 40 g of an aqueous solution containing 10% by weight of polyvinyl alcohol. The mixture was slowly dispersed and mixed in a ball mill at room temperature for 24 hours, whereby a slurry was obtained. The solid substance in the slurry had an average particle size of about 5 μm. Both slurries were mixed, and the mixture was uniformly dispersed and mixed at room temperature for 1 hour, whereby a slurry mixture was prepared. This slurry mixture was coated on one surface of a normal paper of 50 g/m² by means of a wire bar coater (wound wire: 0.35 mm in diameter) in an amount of the coated compound being 1.5 g/m² of the paper. The coated paper was dried in air at room temperature, whereby a heat sensitive record sheet having a substantially colorless heat sensitive layer was obtained. This heat sensitive record sheet will be referred to as No. a.

In the same manner, heat sensitive record sheets No. b to No. o were prepared by using Compounds No. B to No. O.

APPLICATION EXAMPLE 2

To 2.0 g of Compound No. P prepared in Example 16, 20 g of water and 20 g of an aqueous solution containing 10% by weight of polyvinyl alcohol were added. The mixture was slowly dispersed and mixed in a ball mill at room temperature for 24 hours, whereby a colorless slurry was obtained wherein the particle size of the compound was about 3 μm. On the other hand, 7 g of bisphenol A was added to 10 g of water and 40 g of an aqueous solution containing 10% by weight of polyvinyl alcohol. The mixture was slowly dispersed and mixed in a ball mill at room temperature for 24 hour, whereby a slurry was obtained. The solid substance in the slurry had an average particle size of about 5 μm. Both slurries were mixed, and the mixture was uniformly dispersed and mixed at room temperature for 1 hour, whereby a slurry mixture was prepared. This slurry mixture was coated on one surface of a normal paper of 50 g/m² by means of a wire bar coater (wound wire: 0.35 mm in diameter) in an amount of the coated compound being 1.5 g/m² of the paper. The coated paper was dried in air at room temperature, whereby a heat sensitive record sheet having a substantially colorless heat sensitive layer was obtained. This heat sensitive record sheet will be referred to as No. p.

In the same manner, heat sensitive record sheets No. q to No. ab were prepared by using Compounds No. Q to No. AB.

Further, for purpose of comparison, heat sensitive record sheets No. ac, No. ad and No. ae were prepared in the same manner as above by using known 2-anilino-3-methyl-6-diethylamino-fluoran (Compound No. AC), 2-anilino-3-methyl-6-N-methyl-N-cyclohexylamino-fluoran (Compound No. AD) and 2-(2-chlorophenylamino)-6-diethylamino-fluoran (Compound No. AE).

These heat sensitive record sheets were subjected to the following tests.

(1) Color-development performance test

Heat sensitive record sheets No. a to No. ab and comparative sheets No. ac, No. ad and No. ae were heated at a temperature of 150° C. for 5 seconds, whereby the developed color hue, the developed color density and the initial color density were measured by means of Macbeth reflex densitometer RD-514 model with a black filter (Wratten # 106).

(2) Color-development characteristic test

Heat sensitive record sheets No. a to No. ab and comparative sheets No. ac, No. ad and No. ae were heated for color-development within the temparature range of from 70° to 160° C. for 5 seconds, whereby the color density at each temperature was measured in the same manner as in the above test (1), and the color-development initiation tmeperature and the rising for the color-development were calculated from the relationship between the temperature and the color density.

The results of the above-mentioned color-development performance test (1) and the results of the measurement of the color-development values (2) are shown in the following Table.

| | Color-development performance and color-development characteristic values of heat sensitive record sheets | | | | | |
|---|---|---|---|---|---|---|
| | Heat sensitive record sheet | | Color-development performance | | Color-development characteristic values | |
| | Compound No. | Sheet No. | Developed color hue | Developed color density | Color-development initiation temperature (°C.) | Rising for color-development |
| Present Invention | A | a | Purplish black | 1.23 | 78.5 | 6.3 |
| | B | b | Purplish black | 1.20 | 83.2 | 5.6 |
| | C | c | Purplish black | 1.18 | 90.5 | 5.1 |
| | D | d | Bluish black | 1.22 | 85 | 3.6 |
| | E | e | Bluish black | 1.20 | 94 | 9.1 |
| | F | f | Bluish black | 1.16 | 73.5 | 7.3 |
| | G | g | Bluish black | 1.24 | 92.5 | 4.76 |
| | H | h | Black | 1.21 | 75 | 5.8 |
| | I | i | Black | 1.18 | 81.5 | 4.7 |
| | J | j | Greenish black | 1.23 | 81.0 | 3.9 |
| | K | k | Dark green | 1.25 | 78.4 | 4.3 |
| | L | l | Reddish purple | 1.17 | 86.5 | 4.5 |
| | M | m | Reddish purple | 1.15 | 79.3 | 3.9 |
| | N | n | purplish black | 1.20 | 83.0 | 4.6 |
| | O | o | Dark blue | 1.19 | 78.9 | 5.1 |
| | P | p | Bluish black | 1.20 | 75.5 | 6.3 |
| | Q | q | Bluish black | 1.19 | 81.5 | 4.8 |
| | R | r | Bluish black | 1.21 | 93.3 | 5.7 |
| | S | s | Bluish black | 1.24 | 96.0 | 5.9 |
| | T | t | Purplish black | 1.24 | 84.5 | 4.05 |
| | U | u | Bluish black | 1.17 | 78.0 | 4.9 |
| | V | v | Greenish black | 1.16 | 76.5 | 7.7 |
| | W | w | Greenish black | 1.25 | 93.2 | 4.8 |
| | X | x | Greenish black | 1.21 | 81.5 | 5.65 |
| | Y | y | Bluish black | 1.20 | 86.0 | 4.5 |
| | Z | z | Bluish black | 1.23 | 91.0 | 8.9 |
| | AA | aa | Bluish black | 1.17 | 79.7 | 4.1 |
| | AB | ab | Bluish black | 1.23 | 94.5 | 3.9 |
| Comparative | AC | ac | Reddish black | 1.12 | 85 | 1.2 |

-continued

Color-development performance and color-development characteristic values of heat sensitive record sheets

| Heat sensitive record sheet | | Color-development performance | | Color-development characteristic values | |
| --- | --- | --- | --- | --- | --- |
| Compound No. | Sheet No. | Developed color hue | Developed color density | Color-development initiation temperature (°C.) | Rising for color-development |
| Examples AD | ad | Reddish black | 1.10 | 92 | 2.4 |
| AE | ae | Reddish black | 1.06 | 125 | 2.7 |

Note: The color development by heating was conducted by means of Iodiaceta model thermotester (manufactured by French National Fiber Research Institute) at a heating temperature of from 70 to 160° C. for a heating time of 5 seconds under a load of 100 g/cm$^2$.

It is evident from the results shown in the above Table that the heat sensitive record sheets wherein the fluoran compounds of the present invention are used, are far superior in the color-development performance and the developed color characteristics to the comparative heat sensitive record sheets wherein comparative fluoran compounds are used. Thus, the industrial value for practical application of the present invention is considerably high.

We claim:

1. A heat sensitive record sheet which comprises a support sheet and a coated layer on the support sheet comprising a fluoran compound having the formula:

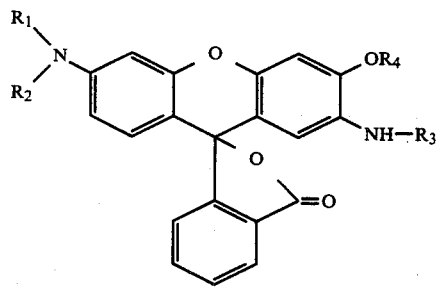

wherein each $R_1$ and $R_2$ is a $C_1$–$C_4$ alkyl group, a cycloalkyl group or an aryl group, or $R_1$ and $R_2$ form together with N a saturated ring, $R_3$ is a benzyl or phenyl group which is unsubstituted or is substituted by a methyl group, ethyl group or halogen atom, and $R_4$ is a $C_1$–$C_4$ alkyl group.

2. The heat sensitive record sheet according to claim 1, wherein said fluoran compound is 2-anilino-3-methoxy-6-di-n-butylamino-fluoran.

3. The heat sensitive record sheet according to claim 1, wherein said fluoran compound is 2-anilino-3-methoxy-6-N-ethyl-N-p-tolylamino-fluoran.

4. The heat sensitive record sheet according to claim 1, wherein said fluoran compound is 2-(2-chlorophenylamino)-3-methoxy-6-di-n-butylamino-fluoran.

5. The heat sensitive record sheet according to claim 1, wherein said fluoran compound is 2-anilino-3-ethoxy-6-di-N-butylamino-fluoran.

6. The heat sensitive record sheet according to claim 1, wherein said fluoran compound is 2-anilino-3-ethoxy-6-N-methyl-N-cyclohexylamino-fluoran.

7. The heat sensitive record sheet according to claim 1, wherein said fluoran compound is 2-anilino-3-ethoxy-6-N-ethyl-N-p-tolylamine-fluoran.

8. A heat sensitive record sheet which comprises a support sheet and a coated layer on the support sheet comprising a fluoran compound having the formula:

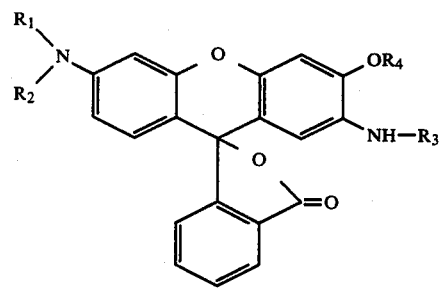

wherein each of $R_1$ and $R_2$ is an ethyl group, a propyl group, a butyl group, a cyclohexyl group, a phenyl group which is unsubstituted or is substituted by a methyl group, an ethyl group or a halogen atom, and $R_3$ is a benzyl group, or a phenyl group which is unsubstituted or is substituted by a methyl group, an ethyl group or a halogen atom.

* * * * *